United States Patent [19]

Collins et al.

[11] 4,031,246

[45] June 21, 1977

[54] ARYLOXYALKYL DIKETONES

[75] Inventors: Joseph C. Collins, East Greenbush; Guy D. Diana, Stephentown, both of N.Y.

[73] Assignee: Sterling Drug Inc., New York, N.Y.

[22] Filed: May 12, 1975

[21] Appl. No.: 576,311

Related U.S. Application Data

[63] Continuation-in-part of Ser. No. 381,406, July 23, 1973, Pat. No. 3,933,837.

[30] Foreign Application Priority Data

July 11, 1974 United Kingdom ............ 30800/74

[52] U.S. Cl. .............................. 424/331; 260/438.1; 260/439 R; 260/590 R; 424/294; 424/295
[51] Int. Cl.² ................... A01N 9/24; A61K 31/12; C07C 49/76
[58] Field of Search ........ 260/590 R, 438.1, 439 R; 424/331, 294, 295

[56] References Cited

UNITED STATES PATENTS

| | | | |
|---|---|---|---|
| 3,541,155 | 11/1970 | D'Amico | 260/590 |
| 3,917,718 | 11/1975 | Collins | 260/590 X |

*Primary Examiner*—Dolph H. Torrence
*Attorney, Agent, or Firm*—Thomas L. Johnson; B. Woodrow Wyatt; Theodore C. Miller

[57] ABSTRACT

Aryloxyalkyl diketones and keto-esters, useful as pesticidal and anti-viral agents, are prepared from an aryloxyalkyl halide and an alkali metal enolate salt of a diketone or keto-ester, or from a haloalkyl-diketone and an alkali metal salt of a phenol.

47 Claims, No Drawings

ARYLOXYALKYL DIKETONES

This application is a continuation-in-part of copending application Ser. No. 381,406, filed July 23, 1973, now U.S. Pat. 3,933,837.

BACKGROUND OF THE INVENTION a. Field of the Invention

This invention relates to aryloxyalkyl diketone and keto-esters, to the preparation thereof and to compositions and methods for the use thereof as pesticidal and anti-viral agents.

b. Description of the Prior Art

Chodnekar et al. U.S. Pat. No. 3,686,222 discloses ethers of the formula R-O-Ar wherein Ar is methylenedioxyphenyl and R is an aliphatic hydrocarbon radical or an epoxide derivative thereof, useful as pesticides having juvenile hormone activity.

Erickson U.S. Pat. No. 3,787,443 discloses ethers of the formula R-O-Ar wherein Ar is methylenedioxyphenyl or other substituted phenyl groups, and R is an aliphatic hydrocarbon radical or an epoxide or episulfide derivative thereof, useful as pesticides having juvenile hormone activity.

Collins U.S. Pat. No. 3,829,475 discloses diketones and keto-esters of the formula RR'CH-Alk-Ar wherein R is acyl, R' is acyl or carboalkoxy, Alk is an alkylene bridge and Ar is phenyl or substituted phenyl, useful as pesticidal and antiviral agents; no aryl ethers are disclosed.

SUMMARY OF THE INVENTION

In a composition of matter aspect, the invention relates to compounds of the formula RR'CH-Alk-O-Ar wherein R is alkanoyl or carbalkoxy, R' is alkanoyl, Alk is alkylene and Ar is phenyl or substituted phenyl, useful as pesticidal or antiviral agents.

In further composition of matter aspects, the invention relates to intermediates of the formula RR'CH-Alk-X where Alk is alkylene and X is Br or I; and intermediates of the formula 2-Cl-4-$CH_3$-O-$C_6H_3$-O-Alk'-Cl where Alk' is alkylene interrupted by an oxygen atom.

In a further composition of matter aspect, the invention relates to a composition for combatting arthropods which comprises an effective amount of a compound of the formula RR'CH-Alk-OAr in admixture with a suitable carrier or diluent.

In a further composition of matter aspect, the invention relates to a composition for combatting viruses which comprises an antivirally effective amount of a compound of the formula RR'CH-Alk-OAr in admixture with a suitable carrier or diluent.

In a process aspect, the invention relates to a process for obtaining the compounds of the invention by treating a compound of the formula X-Alk-O-Ar, where X is bromine or iodine, with a compound of the formula RR'CH$^-$M$^+$ where M$^+$ is an alkali metal cation; or, conversely, reacting a compound of the formula RR'CH-Alk-X with a compound of the formula ArO$^-$M$^+$.

In a further process aspect, the invention relates to a method for combatting arthropods which comprises treating said arthropods with an effective amount of a compound of the formula RR'CH-Alk-OAr in admixture with a suitable carrier or diluent.

In a further process aspect, the invention relates to a method for combatting viruses which comprises contacting the locus of said viruses with an anti-virally effective amount of a compound of the formula RR'CH-Alk-OAr in admixture with a suitable carrier or diluent.

DETAILED DESCRIPTION INCLUSIVE OF PREFERRED EMBODIMENTS

The compounds of the invention are of the structural formula

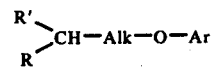

I wherein:

Alk is alkylene of 3 to 10 carbon atoms optionally interrupted by an oxygen atom separated by at least two carbon atoms from the terminal bonds of Alk;

R is alkanoyl of 2 to 6 carbon atoms;

R' is alkanoyl of 2 to 6 carbon atoms or carboalkoxy of 2 to 6 carbon atoms;

and Ar is phenyl or phenyl substituted by one to three substituents selected from the group consisting of alkyl of 1 to 4 carbon atoms, alkoxy of 1 to 4 carbon atoms, alkylthio of 1 to 4 carbon atoms, alkoxyalkoxy of 3 to 6 carbon atoms, hydroxyalkoxy of 2 to 4 carbon atoms, halogen, cyano, nitro, acetyl, sulfo, aminosulfonyl, trifluoromethyl, trifluoromethoxy, hydroxy, benzyloxy, carboxy, carboalkoxy of 2 to 4 carbon atoms, acyloxy of 1 to 10 carbon atoms, dialkylamino where alkyl has from 1 to 4 carbon atoms, and dialkylaminoalkoxy where alkyl has from 1 to 4 carbon atoms and alkoxy has from 2 to 4 carbon atoms.

Also within the scope of the invention are pharmaceutically acceptable heavy metal chelates of the foregoing compounds, wherein the metal is complexed with the carbonyl groups of the diketone or keto-ester moiety. Such metals include copper (valence II), nickel, cobalt and the like.

In the above general formula I, Alk strands for a saturated aliphatic hydrocarbon bridge containing from 3 to 10 carbon atoms. The alkylene bridge may be straight or branched. A preferred class of compounds are those where Alk is straight chain alkylene of 3 to 10 carbon atoms, and if the Alk bridge is branched, it is preferred that it be symmetrical, that is with the branching at the same relative positions from either end of the bridge.

The alkylene bridge, Alk, is optionally interrupted by an oxygen atom separated by at least two carbon atoms from the terminal bonds of Alk. The oxygen atom is preferably in the center of the alkylene bridge, equidistant from the terminal bonds of Alk.

The carbon chains of R and R' can be straight or branched.

When two or three monovalent substitutents are present on the phenyl ring of Ar, they can be the same or different. In the event alkoxyalkoxy is present on the phenyl ring, it is preferred that the two oxygen atoms therein be separated by at least two carbon atoms. It is also preferred that no more than one nitro or sulfo group be present on the phenyl ring.

The compounds of the invention are prepared according to the following reaction sequence:

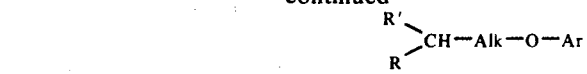

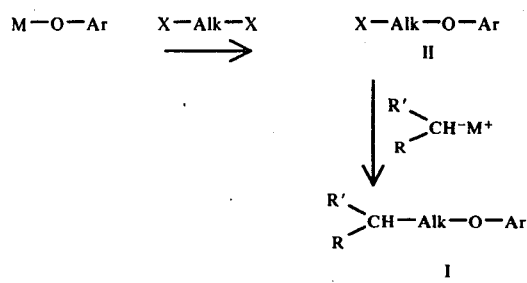

An alkali metal salt of a phenol (HOAr), M-O-Ar, where M is alkali metal, preferably sodium or potassium, is interacted with an alkylene dihalide, X-Alk-X, where X is chlorine, bromine or iodine. The reaction takes place with moderate heating, between about 50° and 100° C. in an inert solvent using equimolar quantities of reactants, or preferably a stoichiometric excess of dihalide to minimize di-ether (Ar-O-Alk-O-Ar) formation. The di-ether that is formed is readily separated from the desired mono-ether (II), because the former is a relatively high melting solid which separates readily from organic solvents while the mono-ether remains in solution.

In the final step, the mono-ether, X-Alk-O-Ar (II), is treated with the alkali metal enolate salt of a diketone or keto-ester of formula RR'CM⁻M⁺, where R and R' have the meanings given hereinabove and M⁺ is an alkali metal cation, preferably lithium, sodium or potassium. The reaction takes place in an inert solvent under anhydrous conditions at ambient temperature or slightly above (25°-70° C.). If the mono-ether, X-Alk-O-Ar, is a chloride (X = Cl), it is preferably converted to the more reactive iodide (X = I) with an alkali metal iodide, prior to the final alkylation step.

If it is desired to obtain compounds of formula I wherein Ar is substituted by one to three hydroxy groups, the reaction between M-OAr and X-Alk-X can be carried out with the corresponding compounds where Ar is substituted by one to three benzyloxy or acyloxy groups. The benzyloxy or acyloxy group or groups can then be cleaved by catalytic hydrogenolysis or hydrolysis, respectively.

It is not, however, essential that phenolic hydroxy groups be protected in the form of ethers or esters at the final stage of the synthesis because the diketone or keto-ester reactant, RR'CH₂, is more acidic than the phenolic hydroxyl; hence the desired alkylation with the iodides or bromides (II, X is I or Br) will take place without affecting any phenolic hydroxy groups which may be present.

Alternatively, in the final step, the alkali metal enolate salt can be replaced by a heavy metal chelate of the diketone or keto-ester. Appropriate heavy metal chelates include the copper, nickel and cobalt chelates.

An alternative approach to the compounds of the invention is depicted in the following reaction sequence:

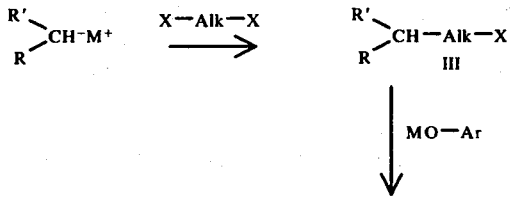

In this alternative approach an alkali metal enolate salt or a heavy metal chelate of a diketone or keto-ester (RR'CH₂) is interacted with an alkylene dihalide, X-Alk-X. The reaction takes place in an inert solvent under anhydrous conditions at ambient temperature or slightly above (20°-70° C.), using equimolar quantities of reactants or a stoichiometric excess of dihalide. The resulting haloalkyl diketone or keto-ester of formula III is then interacted with an alkali metal salt of a phenol (HOAr), which reaction takes place with moderate heating, between about 50° and 100° C. in an inert solvent under anhydrous conditions. In this approach, any free hydroxy groups present in Ar should be protected in the form of the benzyl ether or an ester in order to prevent competing reactions with the haloalkyl diketone.

The intermediates of formula III are novel compounds and within the purview of the invention.

It is preferred to carry out the initial etherification step with a dibromide (X-Alk-X where X is Br) because of the more ready availability of dibromides as compared to diiodides. The resulting bromide (X-Alk-O-Ar or RR'CH-Alk-X where X is Br) can be interacted directly with the alkali metal enolate salt RR'λCH⁻M⁺ or phenolate ArO⁻M⁺, respectively; or if desired converted to the corresponding iodide (X-Alk-O-Ar or RR'CH-Alk-X where X is I) which reacts somewhat more easily with the enolate or phenolate salt than does the bromide. The conversion of II (X = Br) to II (X = I) or III (X = Br) to III (X = I) is effected by heating the former with sodium or potassium iodide in an inert solvent, e.g. acetone.

The dihalides, X-Alk-X, where Alk is branched or oxygen interrupted are preferably symmetrical, that is, the branching or hetero atom is in the same relative position or positions with respect to the terminal halogen atoms, in order to avoid production of mixtures upon ether formation.

It is also possible to employ chlorobromoalkanes as the dihalide reactant, namely, Cl-Alk-Br. The use of such mixed dihalides has the advantage that di-ether formation is eliminated or minimized, since reaction occurs preferentially with the bromine atom, especially if stoichiometric proportions of phenol and dihalide are used. Furthermore, it is possible by this variation in the procedure to obtain compounds with unsymmetrically branched or oxygen interrupted alkylene bridges without producing mixtures. The resulting chloroalkoxy aryl ether, Cl-Alk-O-Ar, or chloroalkyl diketone or keto-ester, Cl-Alk-CHR'R, must then be converted to the corresponding bromo or iodo compound before it will react with the alkali metal phenolate or the alkali metal enolate salt of a diketone or keto-ester, respectively. The chlorobromoalkane starting materials can be prepared by reduction, e.g. with lithium aluminum hydride, of a chloro-ester, Cl-Alk'-COOCH₃, to afford a chloroalkanol, Cl-Alk-OH, followed by replacement of the hydroxy group with bromine, e.g. with phosphorus tribromide.

It is preferred to prepare compounds of formula I where the aryl group is substituted by acyloxy by esterification of the corresponding hydroxy compounds with the appropriate acid halide or acid anhydride. The acyloxy groups are derived from carboxylic acids having from one to about ten carbon atoms, and having a molecular weight less than about 200. Representative of the acyl radicals which can be present are lower-alkanoyl radicals, e.g., formyl, acetyl, propionyl, butyryl, isobutyryl, caproyl, heptanoyl, octanoyl, trimethylacetyl, and the like; carboxy-lower-alkanoyl radicals, e.g., succinyl (β-carboxypropionyl); cycloalkyl-lower-alkanoyl radicals, e.g., β-cylcopentylpropionyl, β-cyclohexylpropionyl, and the like; monocarbocyclic aroyl radicals, e.g., benzoyl, p-toluyl, p-nitrobenzoyl, 3,4,5-trimethoxybenzoyl, and the like; monocarbocyclic aryl-lower-alkanoyl or -alkenoyl radicals, such as phenylacetyl, β-phenylpropionyl, cinnamoyl, and the like; and monocarbocyclic aryloxy-lower-alkanoyl radicals, such as p-chlorophenoxyacetyl, and the like; and amino-lower-alkanoyl, such as glycinyl, alaninyl, diethylaminopropionyl, piperidinopropionyl, pyrrolidinopropionyl, morpholinobutyryl, and the like. When monocarbocyclic aryl groups are present in the ester moieties, monocarbocyclic aryl includes phenyl and phenyl substituted by from one to three lower-alkyl, lower-alkoxy, halogen or nitro groups, which substituents, if plural, can be the same or different. It is preferred that no more than one nitro group be present.

It is preferred to prepare compounds of formula I where the aryl group is substituted by carboxyl (COOH) by hydrolysis of the corresponding compounds of formula I where the aryl group is substituted by carboalkoxy. A sulfo group can be introduced into the aryl group of a compound of formula I by direct sulfonation with sulfuric acid.

It is preferred to prepare compounds of formula I where the aryl group is substituted by dialkylaminoalkoxy by etherification of the corresponding compounds of formula I where the aryl group is substituted by hydroxy, effected by reacting an alkali metal salt of the latter with a dialkylaminoalkyl halide.

Biological evaluation of the compounds of the invention has shown that they posses antiviral activity. They have been found to be effective against one or more of a large variety of RNA and DNA viruses, including Myxoviruses, e.g. influenza types $A_0$, $A_1$, A-2, B; Paramyxoviruses, e.g. parainfluenza types 1, 2, 3, and mumps virus; Picornaviruses, e.g. human rhinoviruses, Coxsackie viruses types A, B, ECHO virsuses, equine rhinoviruses; Reoviruses, types 1, 2, 3; Arboviruses, e.g. equine encephalomyelitis (Eastern, Western and Venezuelan), Semliki Forest virus; miscellaneous RNA viruses, e.g. measles, distemper, respiratory syncytial, rubella, vesicular stomatitis, hepatitis; Herpes viruses, e.g. HSV type I, II, herpesvirus simiae, herpesvirus varicellae, infectious bovine rhinotracheitis, cytomegalovirus, Marek's disease virus, Epstein-Barr virus; Poxviruses, e.g. variola, vaccinia; leukemogenic viruses. Both in vitro and in vivo antiviral activity have been found in the compounds of the invention. The in vitro testing of the compounds showed that they had minimal growth inhibitory concentrations (mic) ranging from about 0.3 to about 50 micrograms per milliliter. The mic values were determined by standard serial dilution procedures.

The compounds of the invention also possess pesticidal activity against arthropod species, as indicated by tests under simulated field conditions in a greenhouse against one or more of the following pest species: yellow mealworm pupae, alfalfa weevil larvae and yellow fever mosquito larvae.

The structure of the compounds of the invention were established by the modes of synthesis, by elementary analysis, and by infrared and nuclear magnetic resonance spectral determinations.

A further aspect of the invention relates to compositions for combatting arthropods by hindering the maturation thereof which comprise an effective amount of at least one compound of formula I in admixture with a suitable carrier or diluent, and to the method of combatting arthropods at any stage of their development by contacting them with said compositions.

The compositions of the invention are effective against insects at any stage of their development short of the final adult form, i.e. at the egg, larval or pupal stages. The compounds can be formulated in conventional manner as solutions, emulsions, suspensions, dusts and aerosol sprays. The pesticide compositions of the invention can contain adjuvants found normally in such preparations, including water and/or organic solvents such as acetone, dimethylformamide, sesame oil, petroleum oils, and the like. Emulsifying and surface active agents may also be added. Dust formulations can contain talc, diatomaceous earth, kaolin, bentonite, calcium carbonate, wood, flour, cork, carbon, and the like. The aerosol sprays contain propellants such as dichlorodifluoromethane. The compounds of this invention can be employed as the sole pesticide component or they can be used in admixture with other compounds having pesticidal utility. While the concentration of active ingredient can vary within rather wide limits, ordinarily the pesticide will comprise not more than about 10%, and preferably about 1% by weight of the composition.

A still further aspect of the invention relates to compositions for combatting viruses which comprise an antivirally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays as foams.

The following examples will further illustrate the invention.

EXAMPLE 1 a. 6-(2-Chloro-4-methoxyphenoxy)hexyl bromide.

A solution of 29.6 g. (0.74 mole) sodium hydroxide pellets in 400 ml. absolute ethanol was prepared with stirring at room temperature and a solution of 108.0 g. (0.68 mole) 2-chloro-4-methoxyphenol in 200 ml. absolute ethanol was added in a fine stream. The solution was stirred at room temperature for 15 minutes, then warmed gently in a steam bath for one-half hour. The reaction mixture was chilled to about 5° C. in an ice bath and 500 g. (2.05 moles) 1,6-dibromohexane was added. The reaction was stirred and allowed to warm to room temperature, then stirred for 6 hours at room temperature and boiled overnight at reflux.

The reaction mixture was evaporated and the residue taken up in ether, washed well with water and evaporated. unreacted 1,6-dibromohexane was collected by distilling the residue at 10 mm. to pot temperature 160°–170° C.; about 280 g. of "water-white" mobile oil was recovered. The pot residue was distilled at .025 mm. via a short path column. A clear, "water-white" fluid was collected, b.p. 110°–115° C. (0.025 mm.), 166.5 g. (76%) of 6-(2-chloro-4-methoxyphenoxy)-hexyl bromide. This material crystallized from hexane just below 25° C.

b.
4-[6-(2-Chloro-4-methoxyphenoxy)hexyl]-3,5-heptanedione [I; Ar is 2-Cl-4-$CH_3OC_6H_3$, Alk is $(CH_2)_6$, R and R' are $CH_3CH_2CO$].

A solution of 74 g. (.23 mole) of 6-(2-chloro-4-methoxyphenoxy)hexyl bromide in 1 liter of acetone was boiled with 35 g. (.23 mole) of sodium iodide at reflux for 3 hours. The acetone was evaporated and the residue was partitioned between ether and water. The ether layer was evaporated in vacuo (warm water bath) and the residual oil comprising 6-(2-chloro-4-methoxyphenoxy)-hexyl iodide was dissolved in 100 ml. dimethylformamide and set aside.

A solution of lithium heptanedione was prepared by treating a well stirred slurry of 4 g. (0.5 mole) of lithium hydride in 500 ml. of diethylformamide with 70 g. (0.55 mole) of 3,5-heptanedione, dropwise over 3/4 hour. Following the addition, the hot reaction mixture was stirred well and warmed in a steam bath for 1 hour and cooled back to room temperature with a cold water bath.

The iodide-dimethylformamide solution was added in a fine stream and the reaction mixture was stirred at 60–70° C. for 36 hours.

The reaction mixture was poured into a mixture of 2 liters of ice, 1 liter of water and 100 ml. of concentrated hydrochloric acid. The ice-mixture was stirred for a few minutes and extracted with 2 × 2 liters of ether. The organic phase was separated, dried over calcium chloride and evaporated in vacuo. The residual oil crystallized from an equal volume of cyclohexane on cooling. The solid was collected, washed with a little cold cyclohexane and recrystallized from 150 ml. cyclohexane, collected and dried in a vacuum oven to give 57 g. (65%) of 4-[6-(2-chloro-4-methoxyphenoxy)hexyl]-3,5-heptanedione as an off-white solid, m.p. 52°–55° C.

In an earlier run, 4-[6-(2-chloro-4-methoxyphenoxy)hexyl]-3,5-heptanedione was obtained in the form of a yellow oil, b.p. 145° C. (0.1 mm.).

Anal. Calcd. for $C_{20}H_{29}ClO_4$: C, 65.12; H, 7.92; Cl, 9.61; Found: C, 65.09; H, 7.92; Cl, 9.44.

IR (oil film) λ μ /max 3.48s + shldrs., 3.57ms (CH); 5.83mss, 5.93s (C=0); 6.27m, 6.37mms, 6.70s, 6.82ms, 6.96m (arom. and CH). NMR (15% $CDCl_3$, internal TMS) δ ppm (Ratio) 6.6–7.0(3) (arom.); 3.96(2) (O-$CH_2$—); 3.76(3) (OMe);

3.66(1) $\left(-C\overset{\frown}{H}\right)$;

2.46(4) (—$CH_2$—CO × 2); 0.9–2.0(10) ($CH_2$ × 5); 1.05(6) (Me triplet × 2).

In Example 1, part b, the lithium heptanedione can be caused to react directly with the 6-(2-chloro-4-methoxyphenoxy)-hexyl bromide without conversion of the latter to the iodide, but yields are not as good as those realized via the iodide.

By replacing the 1,6-dibromohexane in Example 1a by a molar equivalent amount of 1,3-dibromo-2-methylpropane or 1-bromo-3-(2-bromoethyl)octane, and proceeding with the subsequent steps of Example 1a and 1b, there can be obtained, respectively, 4-[3-(2-chloro-4-methoxyphenoxy)-2-methylpropyl]-3,5-heptanedione [I; Ar is 2-Cl-4-$CH_3OC_6H_3$, Alk is $CH_2CH(CH_3)CH_2$, R and R' are $CH_3CH_2CO$], or 4-[5-(2-chloro-4-methoxyphenoxy)-3-pentylpentyl]-3,5-heptanedione [I; Ar is 2-Cl-4-$CH_3OC_6H_3$, Alk is $CH_2CH_2CH(C_5H_{11})CH_2CH_2$, R and R' are $CH_3CH_2CO$].

EXAMPLE 2 a. 6-(2-Chloro-4-methoxyphenoxy)hexyl bromide.

A suspension of 340 g. (2.15 moles) of 2-chloro-4-methoxyphenol, 1560 g. (6.45 moles) of 1,6-dibromohexane and 340 g. (2.46 moles) of anhydrous powdered potassium carbonate in 1.5 liters of acetone was stirred at reflux for 12 hours. The reaction mixture was cooled to room temperature, filtered and the residue was washed with 4 × 400 ml. of acetone. The combined organic fractions were freed of acetone (rotary evaporator) and the residual, pale yellow liquid was distilled in vacuo to a pot temperature of 115° C. at 1 mm. to yield 970 g. (93% recovery) of unreacted 1,6-dibromohexane. Continued distillation at 0.025 mm. afforded 579 g. (84%) of 6-(2-chloro-4-methoxyphenoxy)hexyl bromide.

b.
4-[6-(2-Chloro-4-methoxyphenoxy)hexyl]-3,5-heptanedione [I; Ar is 2-Cl-4-$CH_3OC_6H_3$, Alk is $(CH_2)_6$, R and R' are $CH_3CH_2CO$].

A suspension of 170 g. (0.5 mole, 94% pure) of 6-(2-chloro-4-methoxyphenoxy)hexyl bromide, 41.5 g. (0.125 mole) potassium iodide, 147 g. (1.15 moles) 3,5-heptanedione and 145 g. (1.05 moles) of powdered anhydrous potassium carbonate (dried in vacuo at 100° C. for 2 hours) in 2 liters of acetone was stirred at reflux for 24 hours. One liter of sovent was distilled off and the remainder was poured with stirring into a solution of 4 liters of ice-water containing 160 ml. of conc. hydrochloric acid. The separated yellowish oil which formed a mushy solid was extracted with 3 × 1.5 liters of ether. The combined ether fractions were washed with saturated brine and dried ($MgSO_4$). The ether was distilling in vacuo and the excess 3,5-heptanedione removed at 70° C./0.8 mm. (rotary evaporator) to afford a pale yellow residual oil (196 g.). This residue was crystallized from 350 ml. cyclohexane and washed on the filter with 3 × 100 ml. of cold cyclohexane to yield 130 g. (71%) of 4-[6-(2-chloro-4-methoxyphenoxy)hexyl]-3,5-heptanedione, m.p. 56°–58° C., identical with the compound of Example 1.

The cupric chelate of 4-[6-(2-chloro-4-methoxyphenoxy)-hexyl]-3,5-heptanedione was prepared as follows: to a solution of 14.8 g. of the diketone in 200 ml. of warm methanol was added a solution of 4.5 g. of cupric acetate monohydrate in 40 ml. of water containing 10 ml. of concentrated ammonium hydroxide. The mixture was boiled for 15 minutes and allowed to stand at room temperature for two hours. The solid product was collected, washed with methanol and crystallized from 600 ml. of ethyl acetate to give 13.6 g. of copper chelate, metallic gray-green crystals, m.p. 136°–137° C.

Anal. Calcd. for $C_{40}H_{56}Cl_2CuO_8$: C, 60.11; H, 7.06; Cl, 8.87. Found: C, 60.20; H, 7.15; Cl, 9.25.

In vitro activity of 4-[6-(2-chloro-4-methoxyphenoxy)hexyl]-3,5-heptanedione:

Tissue culture studies:

| Challenge Virus | Minimal Inhibitory Concentration (mcg/ml) |
|---|---|
| Herpes simplex type 1 (Sheely strain) | 6.0 |
| Herpes simplex type 2 (Curtis strain) | 6.0 |
| Herpes simplex type 1 (AMC) | 3.0 |
| Vaccinia virus | 3.0 |
| Human rhinovirus type 2 | 0.7 |
| Human rhinovirus type 14 | 1.5 |
| Human rhinovirus type 17 | 3.0 |
| Respiratory syncytial virus | 3.0 |
| Parainfluenza virus type 3 | 1.5 |
| Equine rhinovirus | 1.5 |
| Poliovirus (YSK strain) | 0.3 |
| Poliovirus (Leon strain) | <0.3 |
| ECHO 9 | 1.5 |
| ECHO 11 | 3.0 |
| Vesicular stomatitis virus | 0.7 |
| Semliki Forest virus | 1.5 |

Organ culture studies:

| Challenge Virus | Tissue | Concn. (mcg/ml) | % Reduction in Virus Yield |
|---|---|---|---|
| Equine rhinovirus | Monkey trachea | 200 | 98 |
| | | 400 | 99.5 |
| Influenza A2 Jap 170 | Ferret trachea | 200 | 99 |
| | | 400 | 99.9 |

In vivo

In of 4-[6-(2-chloro-4-methoxyphenoxy)-hexyl]-3,5-heptanedione:

Intranasal administration at 100 to 200 mg/kg daily in ferrets reduced the titer of influenza A2 Jap 170 virus by 90–99% in the upper respiratory tract.

Keratoconjunctivitis in rabbits caused by infection with herpes simplex virus type 1 (HSV-1, Sheely strain) was effectively suppressed by topical application of 0.5% of the compound in a base of castor oil starting 3 days postinfection. Permanent damage to the eye was prevented.

The following are illustrative formulations of 4-[6-(2-chloro-4-methoxyphenoxy)hexyl]-3,5-heptanedione (identified below as "dione"):

For ophthalmic use:

1) Mineral oil-petrolatum formulation

| | % (weight/weight) |
|---|---|
| Dione | 2.00 |
| Neomycin Sulfate | 1.00 |
| Light Mineral Oil | 33.0 |
| White Petrolatum | 64.0 |
| | 100.0 |

2) 2% Aqueous Dispersion

| | |
|---|---|
| Dione | 2.00 g. |
| Tyloxapol | 0.25 g. |
| Sodium Phosphate | 1.02 g. |
| Sodium Biphosphate | 0.17 g. |
| Sodium Chloride | 0.53 g. |
| Benzalkonium Chloride | 0.10 g. |
| Purified water q.s. ad | 100 ml. |

3) Castor oil ointment

| | % (w/w) |
|---|---|
| Dione | 2.00 |
| Hydrogenated Castor Oil | 4.90 |
| Castor Oil | 93.1 |
| | 100.0 |

For skin infections:
Antiviral Cream

| | % (w/w) |
|---|---|
| Stearic Acid | 10.0 |
| Cetyl Alcohol | 1.00 |
| Castor Oil | 20.0 |
| Sorbitan Stearate | 2.0 |
| PPG Buteth-660 | 5.0 |
| Dione | 2.0 |
| Polysorbate | 1.0 |
| Triethanolamine | 6.0 |
| Purified water q.s. ad | 100.0 |

Aerosol formulation:

| | % (w/w) |
|---|---|
| Dione | 3.8 |
| Dipropylene glycol | 15.0 |
| Trichloromonofluoromethane | 48.7 |
| Dichlorodifluoromethane | 32.5 |
| | 100.0 |

Formulation for intranasal administration:

| | % (Weight per unit volume) |
|---|---|
| Benzalkonium Chloride | 0.040 |
| Sodium Citrate (hydrous) | 0.550 |
| Citric Acid (hydrous) | 0.010 |
| Tyloxapol | 0.125 |
| Sodium Chloride | 0.740 |
| Dione | 3.10 |
| Purified water q.s. ad | 100 |

According to the foregoing procedures starting from the appropriate substituted phenol and alkylene dibromide, the following compounds were prepared:

EXAMPLE 3:

4-[6-(4-Chlorophenoxy)hexyl]-3,5-heptanedione

[I; Ar is 4-$ClC_6H_4$, Alk is $(CH_2)_6$, R and R' are $CH_3CH_2CO$], b.p. 168°–178° C. (0.01 mm.), colorless liquid, prepared from 6-(4-chlorophenoxy)hexyl bromide, b.p. 130°–140° C. (0.05–0.1 mm).

Anal. Calcd. for $C_{19}H_{27}ClO_3$: C, 67.39; H, 8.03; Cl, 10.42. Found: C, 67.59; H, 8.16; Cl, 10.49.

IR (oil film) λ μ $^{max}$ 3.42s + shldrs. (CH); 5.97mss, 5.89s (C=O); 6.28mms, 6.33mms, 6.69s, 6.79–6.90m (arom. and CH).

EXAMPLE 4:

4-[6-(4-Methoxyphenoxy)hexyl]-3,5-heptanedione

[I; Ar is 4-$CH_3OC_6H_4$, Alk is $(CH_2)_6$, R and R' are $CH_3CH_2CO$], b.p. 161°–171° C. (0.01 mm.), yellow crystals, prepared from 6-(4-methoxyphenoxy)hexyl bromide, m.p. 50°–51° C.

Anal. calcd. for $C_{20}H_{30}O_4$: C, 71.82; H, 9.04. Found: C, 71.87; H, 9.09.

IR (oil film) λ μ $^{max}$ 3.44s + shldrs. (CH); 5.81mss, 5.91s (C=O); 6.33m, 6.65s, 6.85mms + shldrs. (arom. and CH).

EXAMPLE 5:

4-(6-Phenyloxyhexyl)-3,5-heptanedione

[I; Ar is $C_6H_5$, Alk is $(CH_2)_6$, R and R' are $CH_3CH_2CO$], b.p. 165° C. (0.05 mm.), colorless semisolid, prepared from 6-phenyloxyhexyl bromide.

Anal. Calcd. for $C_{19}H_{28}O_3$: C, 74.96; H, 9.27 Found: C, 75.14; H, 9.47.

IR (oil film) λ μ $^{max}$ 3.44s + shldrs. (CH); 5.81mss, 5.91s (C=O); 6.28mss, 6.33 shldr., 6.70s, 6.80–6.87m (arom. and CH).

EXAMPLE 6:

4-[6-(4-Benzyloxyphenoxy)hexyl]-3,5-heptanedione

[I; Ar is 4-$C_6H_5CH_2OC_6H_4$, Alk is $(CH_2)_6$, R and R' are $CH_3CH_2CO$], light yellow oil, prepared from 6-(4-benzyloxyphenoxy)hexyl bromide, m.p. 82°–84° C.

Anal. Calcd. for $C_{26}H_{34}O_4$: C, 76.06; H, 8.35. Found: C, 76.09; H, 8.56.

IR (oil film) $\lambda \mu$ $^{max}$ 3.50mss + shldrs., 3.58ms (CH); 5.88s, 5.91mss (C=O); 6.35m, 6.68s, 6.84-6.92mms (arom. and CH).

EXAMPLE 7:

4-[6-(3-Dimethylaminophenoxy)hexyl]-3,5-heptanedione

[I; Ar is 3-$(CH_3)_2NC_6H_4$, Alk is $(CH_2)_6$, R and R' are $CH_3CH_2CO$], dark yellow oil, prepared from 6-(3-dimethylaminophenoxy)hexyl bromide.

Anal. Calcd. for $C_{21}H_{33}NO_3$: C, 72.58; H, 9.57; N, 4.03. Found: C, 72.39; H, 9.71; N, 3.86.

IR (oil film) $\lambda \mu$ $^{max}$ 3.45s + shldrs. (CH); 5.82mss, 5.91s (C=O); 6.24s, 6.42mss, 6.68s, 6.90ms (arom. and CH).

EXAMPLE 8:

4-[7-(4-Benzyloxyphenoxy)heptyl]-3,5-heptanedione

[I; Ar is 4-$C_6H_5CH_2OC_6H_4$, Alk is $(CH_2)_7$, R and R' are $CH_3CH_2CO$], colorless, waxy solid, m.p. 54°–55° C., prepared from 7-(4-benzyloxyphenoxy)heptyl bromide, m.p. 54° C.

Anal. Calcd. for $C_{27}H_{36}O_4$: C, 76.30; H, 8.55. Found: C, 76.22; H, 8.61.

IR (melted solid) $\lambda \mu$ $^{max}$ 3.43s + shldrs., 3.51ms (CH); 5.80mss, 5.90s (C=O); 6.31m + shldrs., 6.65s, 6.83, 6.88ms (arom. and CH).

EXAMPLE 9:

4-[7-(4-Carbethoxyphenoxy)heptyl]-3,5-heptanedione

[I; Ar is 4-$C_2H_5OOCC_6H_4$, Alk is $(CH_2)_7$, R and R' are $CH_3CH_2CO$], yellow oil, b.p. 172°–202° C. (0.008 mm.), prepared from 7-(4-carbethoxyphenoxy)heptyl bromide.

Anal. Calcd. for $C_{23}H_{34}O_5$: C, 70.74; H, 8.78. Found: C, 70.76; H, 8.77.

IR (oil film) $\lambda \mu$ $^{max}$ 3.42mss + shldrs. (CH); 5.85s + shldrs. (C=O); 6.24s, 6.34m, 6.83m + shldrs. (arom. and CH).

EXAMPLE 10:

4-[7-(3-Dimethylaminophenoxy)heptyl]-3,5-heptanedione

[I; Ar is 3-$(CH_3)_2NC_6H_4$, Alk is $(CH_2)_7$, R and R' are $CH_3CH_2CO$], yellow oil, prepared from 7-(3-dimethylaminophenoxy)heptyl bromide.

Anal. Calcd. for $C_{22}H_{35}NO_3$: C, 73.09; H, 9.76; N, 3.87. Found: C, 72,98; H, 9.77; N, 3.89.

IR (oil film) $\lambda \mu$ $^{max}$ 3.44s + shldrs., 3.52mss, 3.58ms (CH); 5.81mss, 5.90s (C=O); 6.24s, 6.37s, 6.68s, 6.85-6.92ms (arom. and CH).

EXAMPLE 11

4-[6-(4-Hydroxyphenoxy)hexyl]-3,5-heptanedione

[I; Ar is 4-$HOC_6H_4$, Alk is $(CH_2)_6$, R and R' are $CH_3CH_2CO$].

A solution of 4.5 g. of 4-[6-(4-benzyloxyphenoxy)hexyl]-3,5-heptanedione (Example 6) in 100 ml. of absolute ethanol was hydrogenated in the presence of 0.4 g. of palladium-on-carbon catalyst at 45 psi. Hydrogenation was complete in 45 minutes. The reaction was repeated with an additional 4.5 g. of benzyl ether starting material, and the runs were combined, filtered and evaporated. The residue was crystallized from 30 ml. of pentane and 60 ml. of ether to give 5.0 g. of 4-[6-(4-hydroxyphenoxy)hexyl]-3,5-heptanedione, m.p. 65°–66° C.

Anal. Calcd. for $C_{19}H_{28}O_4$: C, 71.22; H, 8.80. Found: C, 71.12; H, 8.96.

IR (1/2% KBr) $\lambda \mu$ $^{max}$ 3.00mss (OH); 3.48mss + shldrs. (CH); 5.88s, 5.94ms (C=O); 6.25w, 6.65m, 6.95m (arom. and CH).

EXAMPLE 12:

4-[7-(4-Hydroxyphenoxy)heptyl]-3,5-heptanedione

[I; Ar is 4-$HOC_6H_4$, Alk is $(CH_2)_7$, R and R' are $CH_3CH_2CO$], m.p. 46°–48° C., was prepared by hydrogenolysis of 4-[7-(4-benzyloxyphenoxy)heptyl]-3,5-heptanedione (Example 8).

Anal. Calcd. for $C_{20}H_{30}O_4$: C, 71.82; H, 9.09; Found: C, 71.68; H, 9.24.

IR (1/2% KBr) $\lambda \mu$ $^{max}$ 2.94mss (OH); 3.44mss + shldrs., 3.52ms (CH); 5.83s, 5.91ms (C=O); 6.62s, 6.82m, 6.93mms (arom. and CH).

By a similar hydrogenolysis procedure 4-[4-(3,4-dibenzyloxyphenoxy)butyl]-3,5-heptanedione can be coverted to 4-[4-(3,4-dihydroxyphenoxy)butyl]-3,5-heptanedione [I; Ar is 3,4-$(HO)_2C_6H_3$, Alk is $CH_2CH_2CH_2CH_2$, R and R' are $CH_3CH_2CO$].

EXAMPLE 13

4-[7-(4-Carboxyphenoxy)heptyl]-3,5-heptanedione

[I; Ar is 4-$HOOCC_6H_4$, Alk is $(CH_2)_7$, R and R' are $CH_3CH_2CO$].

A solution of 10.7 g. of 4-[7-(4-carbethoxyphenoxy)-heptyl]-3,5-heptanedione (Example 9) and 3 ml. of concentrated hydrochloric acid in 150 ml. of dioxane was heated at reflux for 48 hours. The solution was treated with activated charcoal, filtered and evaporated to dryness. The residue was taken up in ether and extracted with 10% potassium carbonate solution. The basic extracts were acidified and the acidified mixture extracted with ether. The ether solution was dried and evaporated, and the residue crystallized from ether to give 5.5 g. of 4-[7-(4-carboxyphenoxy)heptyl]-3,5-heptanedione, m.p. 105°–107° C.

Anal. Calcd. for $C_{21}H_{30}O_5$: C, 69.59; H, 8.34. Found: C, 69.50; H, 8.32.

IR (½% KBr) $\lambda \mu$ $^{max}$ 3.42mss + shldrs., 3.52ms (CH); 3.70-4.0m, fine structure (chelate H-bonding); 5.85s, 5.98s + shldrs. (C=O); 6.24s, 6.34m, 6.61m, 6.81m, 6.98 + shldrs. (arom. and CH).

EXAMPLE 14

4-{6-[4-(2-Diethylaminoethoxy)phenoxy]hexyl}-3,5-heptanedione

[I; Ar is 4-$(C_2H_5)_2CH_2CH_2OC_6H_4$, Alk is $(CH_2)_6$, R and R' are $CH_3CH_2CO$].

A mixture of 11 g. (0.034 mole) of 4-[6-(4-hydroxyphenoxy)hexyl]-3,5-heptanedione (Example 11), 4.97 g. (0.034 mole) of 2-diethylaminoethyl chloride and 9.66 g. (0.07 mole) of potassium carbonate in 200 ml. of dimethylformamide was stirred at 25°–30° C. for 3 days. The reaction mixture was concentrated to remove the solvent, and the residue was partitioned between water and ether. The ether layer was washed with water, dried and concentrated. The residue was chromatographed on 280 g. of activated magnesium silicate and eluted with the pentane-benzenemethanol series. Benzene containing 1% methanol brought out 5.5 g. of 4-{6-[4-(2-diethylaminoethoxy)phenoxy]hexyl}-3,5-heptanedione. The latter was dissolved in 30 ml. of absolute ether, and to this was added dropwise 3.3% ethereal hydrochloric acid with stirring until the pH remained acid. The solid material was collected by filtration and dried in vacuo at room temperature. The latter was recrystallized by dissolving it in isopropyl alcohol and adding ether and pentane until the solution became turbid. There was thus obtained 2.0 g. of 4-{6-[4-(2-diethylaminoethoxy)phenoxy]hexyl}-3,5-heptanedione in the form of its hydrochloride salt, m.p. 90–92° C.

Anal. Calcd. for $C_{25}H_{41}NO_4 \cdot HCl$: C, 65.84; H, 9.28; N, 3.07. Found: C, 65.72; H, 9.32; N, 3.16.

IR (3/4% KBr) $\lambda \mu^{max}$ 3.42mss + shldrs. (CH); 3.65–4.35m, fine structure (N+H); 5.83mss + shldrs. (C=O); 6.17w, 6.29w, 6.62s, 6.82ms + shldrs. (arom. and CH).

EXAMPLE 15

4-[6-(4-Benzoyloxyphenoxy)hexyl]-3,5-heptanedione

[I; Ar is 4-$C_6H_5COOC_6H_4$, Alk is $(CH_2)_6$, R and R' are $CH_3CH_2CO$].

Benzoyl chloride (5.05 g.) was added dropwise to a solution of 9.6 g. of 4-[6-(4-hydroxyphenoxy)hexyl]-3,5-heptanedione (Example 11) in 60 ml. of pyridine, held in a cooling bath. The mixture was stirred at room temperature for four hours, then poured into 200 ml. of ice water and allowed to stand for 95 minutes. The reaction mixture was extracted with ether, and the ether extracts were washed with dilute hydrochloric acid, 5% aqueous sodium bicarbonate and with water, and then dried over anhydrous sodium sulfate. The solvent was removed and the residue crystallized from cyclohexane-ether and recrystallized from ether to give 7 g. of 4-[6-(4-benzoyloxyphenoxy)hexyl]-3,5-heptanedione, colorless needles, m.p. 76°–77° C.

Anal. Calcd. for $C_{26}H_{32}O_5$: C, 73.56; H, 7.60; Found: C, 73.56; H, 7.66.

Similarly, there was prepared 4-{6-[4-(4-methoxybenzoyloxy)phenoxy]hexyl}-3,5-heptanedione [I; Ar is 4-(4-$CH_3OC_6H_4COO)C_6H_4$, Alk is $(CH_2)_6$, R and R' are $CH_3CH_2CO$], m.p. 68°–70° C.

Similarly, 4-[6-(4-hydroxyphenoxy)hexyl]-3,5-heptanedione can be caused to react with acetic anhydride, propionic anhydride, caproyl chloride, succinic anhydride, β-cyclopentylpropionyl chloride, 4-nitrobenzoyl chloride, 3,4,5-trimethoxybenzoyl chloride, 4-methylbenzoyl chloride, phenylacetyl chloride or cinnamoyl chloride to give, respectively, the acetate, propionate, caproate, hemisuccinate, β-cyclopentylpropionate, 4-nitrobenzoate, 3,4,5-trimethoxybenzoate, 4-methylbenzoate, phenylacetate or cinnamate ester of 4-[6-(4-hydroxyphenoxy)hexyl]-3,5-heptanedione.

EXAMPLE 16 a. 4-(6-Bromohexyl)-3,5-heptanedione.

A solution of 64.1 g. of 3.5-heptanedione in 200 ml. of dimethylformamide was added over a period of one hour to a suspension of 3.65 g. of lithium hydride in 400 ml. of dimethylformamide. The mixture was stirred for one hour and 488 g. of 1,6-dibromohexane was then added all at once. The reaction mixture was warmed at 60°–70° C. for 24 hours. The volatile solvent was removed and the residue partitioned between water and methylene dichloride. The methylene dichloride solution was concentrated and the residue distilled to give 65.0 g. of 4-(6-bromohexyl)-3,5-heptanedione, b.p. 118°–124° C. (0.005 mm.).

By substituting for the 1,6-dibromohexane the corresponding homologous dibromoalkanes, there were prepared 4-(8-bromooctyl)-3,5-heptanedione, b.p. 136°–139° C. (0.004 mm.); 4-(9-bromononyl)-3,5-heptanedione, b.p. 135°–137° C. (0.004 mm.); and 4-(10-bromodecyl)-3,5-heptanedione, b.p. 157°–159° C. (0.005 mm.).

By selecting the appropriate alkane dibromide and dione or keto-ester, there can be prepared 3-(3-bromopropyl)-2,4-pentanedione, 4-(6-bromohexyl)-2,2,6,6-tetramethyl-3,5-pentanedione, ethyl 2-acetyl-8-bromooctanoate, 4-[2-(2-bromoethoxy)ethyl]-3,5-pentanedione, and the like.

b.

4-[6-(2-Chloro-4-nitrophenoxy)hexyl]-3,5-heptanedione [I; Ar is 2-Cl-4-$O_2NC_6H_3$, Alk is $(CH_2)_6$, R and R' are $CH_3CH_2CO$].

A mixture of 8.7 g. of 2-chloro-4-nitrophenol, 12.5 g. of 4-(6-bromohexyl)-3,5-heptanedione, 225 ml. of 2-butanone, 20.8 g of potassium carbonate and 2 g. of potassium iodide was heated at reflux for 22 hours. The reaction mixture was partitioned between water and chloroform, and the latter solution was washed with saturated sodium chloride solution and dried over anhydrous magnesium sulfate. The product obtained by evaporation of the solvent was chromatographed on silica gel, eluted with hexane-ethyl acetate 6:1 and 4:1, and distilled to give 4.9 g. of 4-[6-(2-chloro-4-nitrophenoxy)hexyl]-3,5-heptanedione as a yellow oil, b.p. 200°–205° C. (0.01 mm.).

Anal. Calcd. for $C_{19}H_{26}ClNO_5$: C, 59.45; H, 6.83; Cl, 9.24. Found: C, 59.77; H, 6.84; Cl, 9.31.

EXAMPLE 17 a. 2-[2-(2-Chloro-4-methoxyphenoxy)ethoxy]ethyl chloride.

To a suspension of 9.6 g. of 50% sodium hydride in 250 ml. of dry dimethylformamide was added in portions 31.6 g. of 2-chloro-4-methoxyphenol. To this mixture was added 143 g. of bis(2-chloroethyl) ether, and the reaction mixture was heated at reflux with stirring for 8 hours. The volatile solvent was removed, the residue partitioned between water and methylene dichloride, and the organic solution washed with water and dried over anhydrous magnesium sulfate. The product was twice distilled to give 2-[2-(2-chloro-4-methoxyphenoxy)ethoxy]ethyl chloride, b.p. 139°–140° C. (0.05 mm.).

Anal. Calcd. for $C_{11}H_{14}Cl_2O_3$: C, 60.11; H, 7.06; Cl, 8.87. Found: C, 60.20; H, 7.15; Cl, 9.25.

Similarly, by replacing the bis(2-chloroethyl) ether with bis(4-chlorobutyl) ether, there was obtained 4-[4-(2-chloro-4-methoxyphenoxy)butoxy]butyl chloride, b.p. 165°–170° C. (0.1 mm.).

Anal. Calcd. for $C_{15}H_{22}Cl_2O_3$: C, 56.08; H, 6.90; Cl, 22.07. Found: C, 56.13; H, 7.01; Cl, 21.78.

b. 2-[2-(2-Chloro-4-methoxyphenoxy)ethoxy]ethyl iodide was prepared from 24.7 g. of the corresponding chloride of part (a) by three hours reflux with 13.5 g. of sodium iodide in 200 ml. of 2-butanone. The crude product was used directly in part (c) below.

c. 4-{2-[2-(2-Chloro-4-methoxyphenoxy)ethoxy]ethyl}-3,5-heptane-dione [I; Ar is 2-Cl-4-CH$_3$OC$_6$H$_3$, Alk is (CH$_2$)$_2$O(CH$_2$)$_2$, R and R' are CH$_3$CH$_2$CO] was prepared from 65.1 g. of the iodide from part (b) and the lithium salt derived from 41.0 g. of 3,5-heptanedione to give 12.1 g. of product, b.p. 168°–172° C. (0.005 mm.).

Anal. Calcd. for C$_{18}$H$_{25}$ClO$_5$: C, 60.59; H, 7.06; Cl, 9.97. Found: C, 60.35; H, 7.24; Cl, 9.85

Similarly, 4-[4-(2-chloro-4-methoxyphenoxy)butoxy]-butyl chloride was converted to 4-{4-[4-(2-chloro-4-methoxyphenoxy)butoxy]butyl}-3,5-heptanedione [I; Ar is 2-Cl-4-CH$_3$OC$_6$H$_3$, Alk is (CH$_2$)$_4$O(CH$_2$)$_4$, R and R' are CH$_3$CH$_2$CO].

EXAMPLE 18

4-[6-(4-Hydroxyphenoxy)hexyl]-3,5-heptanedione 4-morpholinobutanoate.

A suspension of 1 g. of 4-[6-(4-hydroxyphenoxy)hexyl]-3,5-heptanedione (Example 11), 686 mg. of 4-morpholinobutyric acid hydrochloride and 876 mg. of dicyclohexylcarbodiimide in 10 ml. of methylene dichloride was stirred at room temperature for about 16 hours. The solid material (dicyclohexylurea) was removed by filtration, the filtrate concentrated, and the residue triturated with ether. The solid product was dissolved in water and extracted with methylene dichloride. The methylene dichloride extracts were dried and concentrated to give 560 mg. of 4-[6-(4-hydroxyphenoxy)hexyl]-3,5-heptanedione 4-morpholinobutanoate in the form of its hydrochloride salt, m.p. 83°–85° C.

Anal. Calcd. for C$_{27}$H$_{41}$NO$_6$·HCl: C, 63.33; H, 8.27; N, 2.74; Cl, 6.92. Found: C, 63.47; H, 8.55; N, 3.12; Cl, 6.68.

By replacing the 4-morpholinobutyric acid hydrochloride in the foregoing preparation by a molar equivalent amount of glycine hydrochloride, 3-dimethylaminopropionic acid hydrochloride, 3-piperidinopropionic acid hydrochloride or 3-pyrrolidinopropionic acid hydrochloride, there can be obtained, respectively the glycinate, 3-dimethylaminopropionate, 3-piperidinopropionate or 3-pyrrolidinopropionate esters of 4-[6-(4-hydroxyphenoxy)hexyl]-3,5-heptanedione.

EXAMPLE 19

4-{6-[4-(2-Ethoxyethoxy)phenoxy]hexyl}-3,5-heptanedione [I; Ar is 4-CH$_3$CH$_2$OCH$_2$CH$_2$OC$_6$H$_4$, Alk is (CH$_2$)$_6$, R and R' are CH$_3$CH$_2$CO] can be prepared from 3.9 g. of 4-[6-(4-hydroxyphenoxy)hexyl]-3,5-heptanedione (Example 11), 12 g. of 2-bromoethyl ethyl ether, 4 g. of potassium carbonate and 1 g. of potassium iodide in 40 ml. of acetone, heated at reflux 48 hours.

Similarly, by replacing the 2-bromoethyl ethyl ether by a molar equivalent amount of 2-bromoethyl methyl ether or 3-bromopropyl propyl ether there can be obtained, respectively, 4-{6-[4-(2-methoxyethoxy)phenoxy]hexyl}-3,5-heptanedione [I; Ar is 4-CH$_3$OCH$_2$CH$_2$OC$_6$H$_4$, Alk is (CH$_2$)$_6$, R and R' are CH$_3$CH$_2$CO], or 4-{6-[4-(3-propoxypropoxy)phenoxy]hexyl}-3,5-heptanedione [I; Ar is 4-CH$_3$CH$_2$CH$_2$OCH$_2$CH$_2$CH$_2$OC$_6$H$_4$, Alk is (CH$_2$)$_6$, R and R' are CH$_3$CH$_2$CO].

According to the procedures described hereinabove the following compounds were prepared:

EXAMPLE 20:

4-[6-(2-Chloro-4-benzyloxyphenoxy)hexyl]-3,5-heptanedione [I; Ar is 2-Cl-4-C$_6$H$_5$CH$_2$OC$_6$H$_3$, Alk is (CH$_2$)$_6$, R and R' are CH$_3$CH$_2$CO], m.p. 75°–76° C.

Anal. Calcd. for C$_{26}$H$_{33}$ClO$_4$: C, 70.18; H, 7.48; Cl, 7.97. Found: C, 69.97; H, 7.56; Cl, 8.09.

EXAMPLE 21:

4-{6-[4-(4-Methylbenzoyloxy)phenoxy]hexyl}-3,5-heptanedione [I; Ar is 4-(4-CH$_3$C$_6$H$_4$COO)C$_6$H$_4$, Alk is (CH$_2$)$_6$, R and R' are CH$_3$CH$_2$CO], m.p. 65°–66° C.

Anal. Calcd. for C$_{27}$H$_{34}$O$_5$: C, 73.95; H, 7.81. Found: C, 74.03; H, 8.04.

EXAMPLE 22:

4-[6-(2-Chloro-4-hydroxyphenoxy)hexyl]-3,5-heptanedione [I; Ar is 2-Cl-4-HOC$_6$H$_3$, Alk is (CH$_2$)$_6$, R and R' are CH$_3$CH$_2$CO], m.p. 51°–54° C.

Anal. Calcd. for C$_{19}$H$_{27}$ClO$_4$: C, 64.31; H, 7.67; Cl, 9.99. Found: C, 64.23; H, 7.81; Cl, 10.15.

EXAMPLE 23:

4-[6-(2-Bromo-4-methoxyphenoxy)hexyl]-3,5-heptanedione [I; Ar is 2-Br-4-CH$_3$OC$_6$H$_3$, Alk is (CH$_2$)$_6$, R and R' are CH$_3$CH$_2$CO], m.p. 64.5°–66° C.

Anal. Calcd. for C$_{20}$H$_{29}$BrO$_4$: C, 58.11; H, 7.07; Br, 19.33. Found: C, 58.03; H, 7.26; Br, 19.72.

EXAMPLE 24:

4-[6-(3-Chloro-5-methoxyphenoxy)hexyl]-3,5-heptanedione [I; Ar is 3-Cl-5-CH$_3$OC$_6$H$_3$, Alk is (CH$_2$)$_6$, R and R' are CH$_3$CH$_2$CO], b.p. 180°–184° C. (0.006 mm.).

Anal. Calcd. for C$_{20}$H$_{29}$ClO$_4$: C, 65.12; H, 7.92; Cl, 9.61. Found: C, 65.35; H, 7.96; Cl, 9.69.

EXAMPLE 25:

4-[6-(4-Bromo-2-chlorophenoxy)hexyl]-3,5-heptanedione [I; Ar is 4-Br-2-ClC$_6$H$_3$, Alk is (CH$_2$)$_6$, R and R' are CH$_3$CH$_2$CO], b.p. 210°–215° C. (0.007 mm.).

Anal. Calcd. for C$_{19}$H$_{26}$BrClO$_3$: C, 54.62; H, 6.27; Br, 19.13; Cl, 8.49. Found: C, 55.11, 55.07; H, 6.50, 6.61; Br, 17.96; Cl, 8.25.

EXAMPLE 26:

4-[6-(4-Cyanophenoxy)hexyl]-3,5-heptanedione [I; Ar is 4-NCC$_6$H$_4$, Alk is (CH$_2$)$_6$, R and R' are CH$_3$CH$_2$CO], b.p. 205°–210° C. (0.005 mm.).

Anal. Calcd. for C$_{20}$H$_{27}$NO$_3$: C, 72.92; H, 8.26; N, 4.25. Found: C, 73.15; H, 8.35; N, 4.28.

EXAMPLE 27:

4-[6-(2-Fluorophenoxy)hexyl]-3,5-heptanedione [I; Ar is 2-FC$_6$H$_4$, Alk is (CH$_2$)$_6$, R and R' are CH$_3$CH$_2$CO], b.p. 160°–163° C. (0.005 mm.).

Anal. Calcd. for C$_{19}$H$_{27}$FO$_3$: C, 70.78; H, 8.44; F, 5.89. Found: C, 71.06; H, 8.57; F, 6.18.

EXAMPLE 28:

4-[6-(4-Methylthiophenoxy)hexyl]-3,5-heptanedione [I; Ar is 4-CH$_3$SC$_6$H$_4$, Alk is (CH$_2$)$_6$, R and R' are CH$_3$CH$_2$CO], m.p. 63°–64° C.

Anal. Calcd. for C$_{20}$H$_{30}$O$_3$S: C, 68.53; H, 8.63; S, 9.15. Found: C, 68.68; H, 8.73; S, 9.38.

EXAMPLE 29:
4-[6-(3-Iodophenoxy)hexyl]-3,5-heptanedione [I; Ar is 3-IC$_6$H$_4$, Alk is (CH$_2$)$_6$, R and R' are CH$_3$CH$_2$CO], b.p. 193°–198° C. (0.005 mm.).

Anal. Calcd. for C$_{19}$H$_{27}$IO$_3$: C, 53.03; H, 6.32; I, 29.49. Found: C, 53.26; H, 6.32; I, 29.11.

EXAMPLE 30:
4-[6-(2-Chlorophenoxy)hexyl]-3,5-heptanedione [I; Ar is 2-ClC$_6$H$_4$, Alk is (CH$_2$)$_6$, R and R' are CH$_3$CH$_2$CO], yellow oil.

Anal. Calcd. for C$_{19}$H$_{27}$ClO$_3$: C, 67.34; H, 8.03; Cl, 10.46. Found: C, 67.49; H, 7.96; Cl, 10.11.
IR (oil film) $\nu$ (cm$^{-1}$): 3060w, 2980w (arom.); 2940s (—CH$_3$); 2860m (—CH$_2$—); 1728s,

1590m; 1485, 1464, 1442ms; 1278ms + shldr.; 1250ms; 1060ms; 750ms.

EXAMPLE 31:
4-[6-(4-Iodophenoxy)hexyl]-3,5-heptanedione [I; Ar is 4-IC$_6$H$_4$, Alk is (CH$_2$)$_6$, R and R' are CH$_3$CH$_2$CO], m.p. 55°–56° C.

Anal. Calcd. for C$_{19}$H$_{27}$IO$_3$: C, 53.03; H, 6.32; I, 29.49. Found: C, 52.77; H, 6.36; I, 29.12.

EXAMPLE 32:
4-[6-(4-Fluorophenoxy)hexyl]-3,5-heptanedione [I; Ar is 4-FC$_6$H$_4$, Alk is (CH$_2$)$_6$, R and R' are CH$_3$CH$_2$CO], b.p. 160°–165° C. (0.01 mm.).

Anal. Calcd. for C$_{19}$H$_{27}$FO$_3$: C, 70.78; H, 8.44. Found: C, 69.69; H, 8.44.

EXAMPLE 33:
4-[6-(2-Chloro-4-fluorophenoxy)hexyl]-3,5-heptanedione [I; Ar is 2-Cl-4-FC$_6$H$_3$, Alk is (CH$_2$)$_6$, R and R' are CH$_3$CH$_2$CO], b.p. 170°–175° C. (0.005 mm.).

Anal. Calcd. for C$_{19}$H$_{26}$ClFO$_3$: C, 63.95; H, 7.34; Cl, 9.93. Found: C, 63.57; H, 7.32; Cl, 10.04.

EXAMPLE 34:
4-[6-(2,4-Dichlorophenoxy)hexyl]-3,5-heptanedione [I; Ar is 2,4-Cl$_2$C$_6$H$_3$, Alk is (CH$_2$)$_6$, R and R' are CH$_3$CH$_2$CO], b.p. 195°–200° C. (0.005 mm.).

Anal. Calcd. for C$_{19}$H$_{26}$Cl$_2$O$_3$: C, 61.13; H, 7.02; Cl, 18.99. Found: C, 61.46; H, 7.05; Cl, 18.96.

EXAMPLE 35:
4-[6-(2-Trifluoromethylphenoxy)hexyl]-3,5-heptanedione [I; Ar is 2-CF$_3$C$_6$H$_4$, Alk is (CH$_2$)$_6$, R and R' are CH$_3$CH$_2$CO], b.p. 165°–166° C. (0.005 mm.).

Anal. Calcd. for C$_{20}$H$_{27}$F$_3$O$_3$: C, 64.50; H, 7.31; F, 15.30. Found: C, 64.12; H, 7.24; F, 15.48.

EXAMPLE 36:
4-[7-(2-Chloro-4-methoxyphenoxy)heptyl]-3,5-heptanedione [I; Ar is 2-Cl-4-CH$_3$OC$_6$H$_3$, Alk is (CH$_2$)$_7$, R and R' are CH$_3$CH$_2$CO], b.p. 195°–196° C. (0.005 mm.).

Anal. Calcd. for C$_{21}$H$_{31}$ClO$_4$: C, 65.87; H, 8.16; Cl, 9.26. Found: C, 65.43; H, 8.12; Cl, 9.70.

EXAMPLE 37:
4-[6-(2-Iodophenoxy)hexyl]-3,5-heptanedione [I; Ar is 2-IC$_6$H$_4$, Alk is (CH$_2$)$_6$, R and R' are CH$_3$CH$_2$CO], b.p. 195°–198° C. (0.005 mm.).

Anal. Calcd. for C$_{19}$H$_{27}$IO$_3$: C, 53.03; H, 6.32; I, 29.49. Found: C, 53.01; H, 6.43; I, 29.09.

EXAMPLE 38: Ethyl 2-acetyl-9-(2-chloro-4-methoxyphenoxy)-nonanoate
[I; Ar is 2-Cl-4-CH$_3$OC$_6$H$_3$, Alk is (CH$_2$)$_7$, R is CH$_3$CO, R' is CH$_3$CH$_2$OCO], b.p. 205°–206° C. (0.03 mm.).

Anal. Calcd. for C$_{20}$H$_{29}$ClO$_5$: C, 62.41; H, 7.59; Cl, 9.21. Found: C, 62.12; H, 7.61; Cl, 9.29.

EXAMPLE 39:
3-[7-(2-Chloro-4-methoxyphenoxy)heptyl]-2,4-pentanedione [I; Ar is 2-Cl-4-CH$_3$OC$_6$H$_3$, Alk is (CH$_2$)$_7$, R and R' are CH$_3$CO], b.p. 189°–191° C. (0.005 mm.).

Anal. Calcd. for C$_{19}$H$_{27}$ClO$_4$: C, 64.31; H, 7.67; Cl, 9.99. Found: C, 64.31; H, 7.83; Cl, 9.90.

EXAMPLE 40:
4-[6-(3-Trifluoromethylphenoxy)hexyl]-3,5-heptanedione [I; Ar is 3-F$_3$CC$_6$H$_4$, Alk is (CH$_2$)$_6$, R and R' are CH$_3$CH$_2$CO], b.p. 153°–155° C. (0.005 mm.).

Anal. Calcd. for C$_{20}$H$_{27}$F$_3$O$_3$: C, 64.50; H, 7.31; F, 15.30. Found: C, 63.84, 64.07; H 7.20, 7.43; F, 15.83, 15.33.

EXAMPLE 41:
4-[6-(4-Nitrophenoxy)hexyl]-3,5-heptanedione [I; Ar is 4-O$_2$NC$_6$H$_4$, Alk is (CH$_2$)$_6$, R and R' are CH$_3$CH$_2$CO], yellow oil.

Anal. Calcd. for C$_{19}$H$_{27}$NO$_5$: C, 65.31; H, 7.79; N, 4.01. Found: C, 66.26, 65.97 H, 8.08, 8.10; N, 3.88.
IR (oil film) $\nu$ (cm$^{-1}$): 3110w, 3080w, 2975w (arom.); 2940s (—CH$_3$); 2860m (—CH$_2$—); 1723ms,

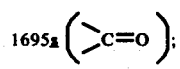

1605m; 1950s; 1510s; 1335vs; 1260vs; 1170m; 1110ms; 845ms; 750ms; 650ms.
Nuclear Magnetic Resonance (NMR) [20% CDCl$_3$; internal tetramethylsilane (TMS)] $\delta$ ppm (Ratio): 8.32($\alpha$); 6.85(2) (arom. CH); 4.08(2) (O-CH$_2$); 3.70(1) [—CH=(CO—)$_2$]; 2.50(4) (—CO—CH$_2$—CH$_3$); 1.04(6) (—COCH$_2$—CH$_3$).

EXAMPLE 42:
4-[8-(2-Chloro-4-methoxyphenoxy)octyl]-3,5-heptanedione [I; Ar is 2-Cl-4-CH$_3$OC$_6$H$_3$, Alk is (CH$_2$)$_8$, R and R' are CH$_3$CH$_2$CO], b.p. 199°–202° C. (0.02 mm.).

Anal. Calcd. for C$_{22}$H$_{33}$ClO$_4$: C, 66.57; H, 8.38; Cl, 8.93. Found: C, 66.81; H, 8.49; Cl, 9.01.

EXAMPLE 43:
3-[8-(2-Chloro-4-methoxyphenoxy)octyl]-2,4-pentanedione [I; Ar is 2-Cl-4-CH$_3$OC$_6$H$_3$, Alk is (CH$_2$)$_8$, R and R' are CH$_3$CO], b.p. 180°–182° C. (0.005 mm.).

Anal. Calcd. for C$_{20}$H$_{29}$ClO$_4$: C, 65.12; H, 7.92; Cl, 9.61. Found: C, 65.24; H, 8.08; Cl, 9.83.

EXAMPLE 44:
4-[9-(2-Chloro-4-methoxyphenoxy)nonyl]-3,5-heptanedione [I; Ar is 2-Cl-4-CH$_3$OC$_6$H$_3$, Alk is (CH$_2$)$_9$, R and R' are CH$_3$CH$_2$CO], b.p. 206°–208° C. (0.03 mm.).

Anal. Calcd. for C$_{23}$H$_{35}$ClO$_4$: C, 67.22; H, 8.58; Cl, 8.63. Found: C, 67.38; H, 8.72; Cl, 8.68.

EXAMPLE 45:
3-[9-(2-Chloro-4-methoxyphenoxy)nonyl]-2,4-pentanedione [I; Ar is 2-Cl-4-CH$_3$OC$_6$H$_3$, Alk is (CH$_2$)$_9$, R and R' are CH$_3$CO], b.p. 190°–193° C. (0.01 mm.).

Anal. Calcd. for C$_{21}$H$_{31}$ClO$_4$: C, 65.87; H, 8.16; Cl, 9.26. Found: C, 66.74; H, 8.40; Cl, 9.42.

EXAMPLE 46:
4-[4-(2-Chloro-4-methoxyphenoxy)butyl]-3,5-heptanedione [I; Ar is 2-Cl-4-CH$_3$OC$_6$H$_3$, Alk is (CH$_2$)$_4$, R and R' are CH$_3$CH$_2$CO], b.p. 191°–193° C. (0.06 mm.).

Anal. Calcd. for C$_{18}$H$_{25}$ClO$_4$: C, 63.43; H, 7.39; Cl, 10.40. Found: C, 63.66; H, 7.30; Cl, 10.54.

EXAMPLE 47:
4-[5-(2-Chloro-4-methoxyphenoxy)pentyl]-3,5-heptanedione [I; Ar is 2-Cl-4-CH$_3$OC$_6$H$_3$, Alk is (CH$_2$)$_5$, R and R' are CH$_3$CH$_2$CO], b.p. 195°–197° C. (0.06 mm.).

Anal. Calcd. for C$_{19}$H$_{27}$ClO$_4$: C, 64.31; H7.67; Cl, 9.99. Found: C, 64.54; H, 7.67; Cl, 10.03.

EXAMPLE 48: Ethyl
2-acetyl-11-(2-chloro-4-methoxyphenoxy)-undecanoate [I; Ar is 2-Cl-4-CH$_3$OC$_6$H$_3$, Alk is (CH$_2$)$_9$, R is CH$_3$CO, R' is CH$_3$CH$_2$OCO], golden yellow oil.

Anal. Calcd. for C$_{22}$H$_{33}$ClO$_5$: C, 63.99; H, 8.06; Cl, 8.59. Found: C, 64.55, 64.49; H, 8.18, 8.20; Cl, 8.91. IR (oil film) $\nu$ (cm$^{-1}$): 3070vw, 2995sh, 2985sh (arom.), 2930s (—CH$_3$); 2850ms (—CH$_2$—); 1738s, 1720s (C=O); 1595s; 1270ms; 1210s; 1050ms +shldr. NMR (20% CDCl$_3$; internal TMS) $\delta$ ppm (Ratio): 6.9(3) (arom.); 4.25 (2 of 8) (O-CH$_2$-CH$_3$); 3.98 (2 of 8) (—O—CH$_2$—CH$_2$—); 3.77 (3 of 8) (O—CH$_3$); 3.42 (1 of 8)

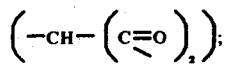

2.22(3) (CH$_3$—C=O).

EXAMPLE 49:
3-[4-(2-Chloro-4-methoxyphenoxy)butyl]-2,4-pentanedione [I; Ar is 2-Cl-4-CH$_3$OC$_6$H$_3$, Alk is (CH$_2$)$_4$, R and R' are CH$_3$CO], b.p. 178°–181° C. (0.035 mm.).

Anal. Calcd. For C$_{16}$H$_{21}$ClO$_4$: C, 61.44; H, 6.77; Cl, 11.33. Found: C, 61.40; H, 6.69; Cl, 11.24.

EXAMPLE 50:
3-[5-(2Chloro-4-methoxyphenoxy)pentyl]-2,4-pentanedione [I; Ar is 2-Cl-4-CH$_3$OC$_6$H$_3$, Alk is (CH$_2$)$_5$, R and R' are CH$_3$CO], b.p. 177°–180° C. (0.02 mm.).

Anal. Calcd. for C$_{17}$H$_{23}$ClO$_4$: C, 62.48; H, 7.09; Cl, 10.85. Found: C, 62.64; H, 7.15; Cl, 10.79.

EXAMPLE 51: Ethyl
2-acetyl-6-(2-chloro-4-methoxyphenoxy)hexanoate [I; Ar is 2-Cl-4-CH$_3$OC$_6$H$_3$, Alk is (CH$_2$)$_4$, R is CH$_3$CO, R' is CH$_3$CH$_2$OCO], b.p. 190°–192° C. (0.12 mm.).

Anal. Calcd. for C$_{17}$H$_{23}$ClO$_5$: C, 59.56; H, 6.76; Cl, 10.34 Found: C, 59.71; H, 6.85; Cl, 10.28.

EXAMPLE 52: Ethyl
2-acetyl-7-(2-chloro-4-methoxyphenoxy-heptanoate [I; Ar is 2-Cl-4-CH$_3$OC$_6$H$_3$, Alk is (CH$_2$)$_5$, R is CH$_3$CO, R' is CH$_3$CH$_2$OCO], b.p. 198°–199° C. (0.13 mm.).

Anal. Calcd. for C$_{18}$H$_{25}$ClO$_5$: C, 60,59; H, 7.06; Cl, 9.94. Found: C, 60.58; H, 6.98; Cl, 10.05.

EXAMPLE 53:
4-[10-(2-Chloro-4-methoxyphenoxy)decyl]-3,5-heptanedione [I; Ar is 2-Cl-4-CH$_3$OC$_6$H$_3$, Alk is (CH$_2$)$_{10}$, R and R' are CH$_3$CH$_2$CO], b.p. 224°–226° C. (0.07 mm.).

Anal. Calcd. for C$_{24}$H$_{37}$ClO$_4$: C, 67.83; H, 8.78; Cl, 8.34. Found: C, 67.78; H, 8.82; Cl, 8.24.

EXAMPLE 54:
3-[10-(2-Chloro-4-methoxyphenoxy)decyl]-2,4-pentanedione [I; Ar is 2-Cl-4-CH$_3$OC$_6$H$_3$, Alk is (CH$_2$)$_{10}$, R and R' are CH$_3$CO], b.p. 216°–218° C. (0.03 mm.).

Anal. Calcd. for C$_{22}$H$_{33}$ClO$_4$: C, 66.57; H, 8.38; Cl, 8.93. Found: C, 66.51; H, 8.41; Cl, 9.06.

EXAMPLE 55: Ethyl
2-acetyl-12-(2chloro-4-methoxyphenoxy)dodecanoate [I; Ar is 2-Cl-4-CH$_3$OC$_6$H$_3$, Alk is (CH$_2$)$_{10}$, R is CH$_3$CO, R' is CH$_3$CH$_2$OCO], golden yellow oil.

Anal. Calcd. for C$_{23}$H$_{35}$ClO$_5$: C, 64.70; H, 8.26; Cl, 8.30. Found: C, 64.99; H, 8.39; Cl, 8.50.

IR (oil film) $\nu$(cm$^{-1}$): 3060vw, 3000sh, 2985sh (arom.); 2920s (CH$_3$); 2850ms (—CH$_2$—); 1740ms, 1715ms (C=O); 1495s; 1270ms, 1210ms; 1050ms = shldr.

EXAMPLE 56:
4-[6-(2,6-Dichlorophenoxy)hexyl]-3,5-heptanedione [I; Ar is 2,6-Cl$_2$C$_6$H$_3$, Alk is (CH$_2$)$_6$, R and R' are CH$_3$CH$_2$CO], b.p. 185°–190° C. (0.005 mm.).

Anal. Calcd. for C$_{19}$H$_{26}$Cl$_2$O$_3$: C, 61.13; H, 7.02; Cl, 18.99. Found: C, 60.93; H, 6.88; Cl, 19.09.

EXAMPLE 57: Ethyl
2-acetyl-8-(2-chloro-4-methoxyphenoxy)octanoate [I; Ar is 2-Cl-4-CH$_3$OC$_6$H$_3$, Alk is (CH$_2$)$_6$, R is CH$_3$CO, R' is CH$_3$CH$_2$OCO], light yellow oil.

Anal. Calcd. for C$_{19}$H$_{27}$ClO$_5$: C, 61.53; H, 7.34; Cl, 9.56. Found: C, 61.31; H, 7.46; Cl, 9.79.

IR (oil film) $\nu$ (cm$^{-1}$): 3060vw, 3000sh, 2985sh (arom.); 2940ms (CH$_3$); 2860m (—CH$_2$—); 1740ms; 1720ms (C=O); 1495s; 1270ms; 1210ms; 1050ms + shldr.

NMR (20% CDCl$_3$; internal TMS) $\delta$ ppm (Ratio); 6.68–70(3) (arom.); 4.16 (2 of 8) (O—CH$_2$—CH$_3$); 3.92 (2 of 8) (—O—CH$_2$—CH$_2$—); 3.70 (3of 8) (—OCH$_3$); 3.38 (1 of 8) (—CH—(CO—)$_2$); 2.16 (3) (—CO—CH$_3$); 1.22 (3 of 16) (—CH$_2$CH$_3$).

EXAMPLE 58:
4-[8-(4-Carbethoxyphenyl)octyl]-3,5-heptanedione [I; Ar is 4-$C_2H_5OOOCC_6H_4$, Alk is $(CH_2)_8$, R and R' are $CH_3CH_2CO$], b.p. 219°–221° C. (0.008 mm.).

Anal. Calcd. for $C_{24}H_{36}O_5$: C, 72.26; H, 8.97. Found: C, 70.88; H, 8.94.

EXAMPLE 59:
4-[9-(4-Carbethoxyphenoxy)nonyl]-3,5-heptanedione [I; Ar is 4-$C_2H_5OOCC_6H_4$, Alk is $(CH_2)_9$, R and R' are $CH_3CH_2CO$], m.p. 65°–66° C.

Anal. Calcd. for $C_{25}H_{38}O_5$: C, 71.74; H, 9.15. Found: C, 72.10; H, 9.30.

EXAMPLE 60:
4-[6-(4-Ethylphenoxy)hexyl]-3,5-heptanedione [I; Ar is 4-$C_2H_5C_6H_4$, Alk is $(CH_2)_6$, R and R' are $CH_3CH_2CO$], b.p. 159°–161° C. (0.005 mm.).

Anal. Calcd. for $C_{21}H_{32}O_3$: C, 75.86; H, 9.70. Found: C, 75.93; H, 9.94.

EXAMPLE 61:
4-[6-(4-Carbethoxyphenoxy)hexyl]-3,5-heptanedione [I; Ar is 4-$C_2H_5OOCC_6H_4$, Alk is $(CH_2)_6$, R and R' are $CH_3CH_2CO$], m.p. 47°–48° C.

Anal. Calcd. for $C_{22}H_{32}O_5$: C, 70.19; H, 8.57. Found: C, 70.33; H, 8.70.

EXAMPLE 62:
4-[8-(4-Benzyloxyphenoxy)octyl]-3,5-heptanedione [I; Ar is 4-$C_6H_5CH_2OC_6H_4$, Alk is $(CH_2)_8$, R and R' are $CH_3CH_2CO$], m.p. 67°–68° C.

Anal. Calcd. for $C_{28}H_{38}O_4$: C, 76.68; H, 8.73. Found: C, 76.97; H, 8.94.

EXAMPLE 63:
4-[10-(4-Benzyloxyphenoxy)decyl]-3,5-heptanedione [I; Ar is 4-$C_6H_5CH_2OC_6H_4$, Alk is $(CH_2)_{10}$, R and R' are $CH_3CH_2CO$], m.p. 70°–71° C.

Anal. Calcd. for $C_{30}H_{42}O_4$: C, 77.21; H, 9.07. Found: C, 77.47; H, 9.09.

EXAMPLE 64:
4-[6-(2,4,6-Triiodophenoxy)hexyl]-3,5-heptanedione [I; Ar is 2,4,6-$I_3$-$C_6H_2$, Alk is $(CH_2)_6$, R and R' are $CH_3CH_2CO$], m.p. 70°–73° C.

Anal. Calcd. for $C_{19}H_{25}I_3O_3$: C, 33.46; H, 3.69; I, 55.81. Found: C, 33.68; H, 3.80; I, 56.36, 56.20.

EXAMPLE 65:
4-[6-(4-Methoxy-2-nitrophenoxy)hexyl]-3,5-heptanedione [I; Ar is 2-$O_2N$-4-$CH_3OC_6H_3$, Alk is $(CH_2)_6$, R and R' are $CH_3CH_2CO$], m.p. 63°–64° C.

Anal. Calcd. for $C_{20}H_{29}NO_6$: C, 63.31; H, 7.70; N, 3.69. Found: C, 63.36; H, 7.92; N, 3.68.

EXAMPLE 66:
4-[6-(2,3,4,5,6-Pentafluorophenoxy)hexyl]-3,5-heptanedione [I; Ar is 2,3,4,5,6-$F_5C_6$, Alk is $(CH_2)_6$, R and R' are $CH_3CH_2CO$], b.p. 135°–138° C. (0.005 mm.).

Anal. Calcd. for $C_{19}H_{23}F_5O_3$: C, 57.87; H, 5.88; F, 24.09. Found: C, 57.85; H, 5.93; F, 23.02 23.83.

EXAMPLE 67:
4-[6-(3-Nitrophenoxy)hexyl]-3,5-heptanedione [I; Ar is 3-$O_2NC_6H_4$, Alk is $(CH_2)_6$, R and R' are $CH_3CH_2CO$], m.p. 46°–47° C.

Anal. Calcd. for $C_{19}H_{27}NO_5$: C, 65.31; H, 7.79; N, 4.01. Found: C, 65.13; H, 7.84; N, 4.05.

EXAMPLE 68:
4-[6-(2-Nitrophenoxy)hexyl]-3,5-heptanedione [I; Ar is 2-$O_2NC_6H_4$, Alk is $(CH_2)_6$, R and R' are $CH_3CH_2CO$], orange oil.

Anal. Calcd. for $C_{19}H_{27}NO_5$: C, 65.31; H, 7.79; N, 4.01. Found: C, 65.48; H, 7.80; N, 3.93.

IR (oil film) $\nu$ (cm$^{-1}$): 3080vw, 2980vw (arom.); 2940ms ($CH_3$); 2860m ($-CH_2-$); 1760ms,

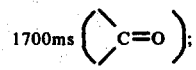
1700ms $\left(\begin{array}{c}\diagup\\\diagdown\end{array}C=O\right)$;

1610ms; 1525ms; 1350ms; 1280ms; 1255ms; 860m; 750ms.

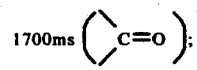
1700ms $\left(\begin{array}{c}\diagup\\\diagdown\end{array}C=O\right)$;

EXAMPLE 69:
4-[8-(4-Carboxyphenoxy)octyl]-3,5-heptanedione [I; Ar is 4-$HOOCC_6H_4$, Alk is $(CH_2)_8$, R and R' are $CH_3CH_2CO$], m.p. 102°–104° C.

Anal. Calcd. for $C_{22}H_{32}O_5$: C, 70.19; H, 8.57. Found: C, 70.66; H, 8.58.

EXAMPLE 70:
4[8-(4-Hydroxyphenoxy)octyl]-3,5-heptanedione[I; Ar is 4-$HOC_6H_4$, Alk is $(CH_2)_8$, R and R' are $CH_3CH_2CO$], m.p. 45-46° C.

Anal. Calcd. for $C_{21}H_{32}O_4$: C, 72.38; H, 9.26. Found: C, 72.31; H, 9.45.

EXAMPLE 71:
4-[10-(4-Hydroxyphenoxy)decyl]-3,5-heptanedione [I; Ar is 4-$HOC_6H_4$, Alk is $(CH_2)_{10}$, R and R' are $CH_3CH_2CO$], m.p. 70–71° C.

Anal. Calcd. for $C_{23}H_{36}O_4$: C, 73.37; H, 9.64. Found; C, 73.42; H, 9.91.

EXAMPLE 72:
4- 8-[4-(2-Diethylaminoethoxy)phenoxy]octyl -3,5-heptanedione [I; Ar is 4-[$(C_2H_5)_2NCH_2CH_2O$]$C_6H_4$, Alk is $(CH_2)_8$, R and R' are $CH_3CH_2CO$], b.p. 208–209° C. (0.005 mm.).

Anal. Calcd. for $C_{27}H_{45}NO_4$: C, 72.44; H, 10.13; N, 3.13. Found: C, 71.96; H, 10.19; N, 3.42. 72.01 10.22

EXAMPLE 73:
4-[6-(4-Aminosulfonylphenoxy)hexyl]-3,5-heptanedione [I; Ar is 4-$NH_2SO_2C_6H_4$, Alk is $(CH_2)_6$, R and R' are $CH_3CH_2CO$], m.p. 86°–87° C.

Anal. Calcd. for $C_{19}H_{29}NO_5S$: C, 59.51; H, 7.62; N, 3.65; S, 8.36. Found: C, 59.18; H, 7.61; N, 3.67; S, 8.37.

EXAMPLE 74:
4-[6-(2-Chloro-4-methoxyphenoxy)hexyl]-2,2,6,6-tetramethyl-3,5-heptanedione [I; Ar is 2-Cl$_4$CH$_3$OC$_6$H$_3$, Alk is (CH$_2$)$_6$, R and R' are (CH$_3$)$_3$COO], m.p. 45°–46° C.

Anal. Calcd. for C$_{24}$H$_{37}$ClO$_4$: C, 67.82; H, 8.77; Cl, 8.34. Found: C, 67.64; H, 8.84; Cl, 8.53.

EXAMPLE 75:
3-[6-(2-Chloro-4-methoxyphenoxy)hexyl]-2,4-pentanedione ]I; Ar is 2-Cl-4-CH$_3$OC$_6$H$_3$, Alk is (CH$_2$)$_6$, R and R' are CH$_3$CO], b.p. 185°–190° C. (0.007 mm.).

Anal. Calcd. for C$_{18}$H$_{25}$ClO$_4$: C, 63.43; H, 7.39; Cl, 10.40. Found: C, 63.59; H, 7.33; Cl, 10.42.

EXAMPLE 76:
4-[6-(4-Acetyl-2-methoxyphenoxy)hexyl]-3,5-heptanedione [I; Ar is 2-CH$_3$O-4-CH$_3$COC$_6$H$_3$, Alk is (CH$_2$)$_6$, R and R' are CH$_3$CH$_2$CO], m.p. 59°–60° C.

Anal. Calcd. for C$_{22}$H$_{32}$O$_5$: C, 70.19; H, 8.57. Found: C, 70.42; H, 8.50.

EXAMPLE 77:
4-[6-(4-Carboxyphenoxy)hexyl]-3,5-heptanedione [I; Ar is 4-HOOCC$_6$H$_4$, Alk is (CH$_2$)$_6$, R and R' are CH$_3$CH$_2$CO], m.p. 99°–101° C.

Anal. Calcd. for C$_{20}$H$_{28}$O$_5$: C, 68.94; H, 8.10. Found: C, 69.32; H, 8.36.

EXAMPLE 78:
4-]9-(4-Benzyloxyphenoxy)nonyl]-3,5-hepetanedione [I; Ar is 4-C$_6$H$_5$CH$_2$OC$_6$H$_4$, Alk is (CH$_2$)$_9$, R and R' are CH$_3$CH$_2$CO], m.p. 69°–71° C.

Anal. Calcd. for C$_{29}$H$_{40}$O$_4$: C, 76.95; H, 8.91. Found: C, 76.77; H, 8.84.

EXAMPLE 79:
4-[6-(2-Chloro-4-carbomethoxyphenoxy)hexyl]-3,5-heptanedione [I; Ar is 2-Cl-4-CH$_3$OOCC$_6$H$_3$, Alk is (CH$_2$)$_6$, R and R' are CH$_3$CH$_2$CO], b.p. 205°–210° C. (0.03 mm.).

Anal. Calcd. for C$_{21}$H$_{29}$ClO$_5$: C, 63.54; H, 7.36; Cl, 8.93. Found: C, 63.53; H, 7.31; Cl, 8.92.

EXAMPLE 80:
4-[9-(4-Hydroxyphenoxy)nonyl]-3,5-heptanedione [I; Ar is 4-HOC$_6$H$_4$, Alk is (CH$_2$)$_9$, R and R' are CH$_3$CH$_2$CO], m.p. 61°–62° C.

Anal. Calcd. for C$_{22}$H$_{34}$O$_4$: C, 72.89; H, 9.45 Found: C, 72.74; H, 9.34.

EXAMPLE 81:
4-[6-(2,5-Dichloro-4-methoxyphenoxy)hexyl]-3,5-heptanedione [I; Ar is 2,6-Cl$_2$-4-CH$_3$OC$_6$H$_2$, Alk is (CH$_2$)$_6$, R and R' are CH$_3$CH$_2$CO], b.p. 190°–195° C. (0.03 mm.).

Anal. Calcd. for C$_{20}$H$_{28}$Cl$_2$O$_4$: C, 59.56; H, 7.00; Cl, 17.58. Found: C, 59.59; H, 6.91; Cl, 17.45.

EXAMPLE 82:
4-[9-(4-Carbomethoxyphenoxy)nonyl]-3,5-heptanedione [I; Ar is 4-CH$_3$OOCC$_6$H$_4$, Alk is (CH$_2$)$_9$, R and R' are CH$_3$CH$_2$CO], colorless needles, m.p. 76°–77° C.

Anal. Calcd. for C$_{24}$H$_{36}$O$_5$: C, 71.26; H, 8.97. Found: C, 71.53; H, 9.06.

EXAMPLE 83:
4-[10-(4-Carbomethoxyphenoxy)decyl]-3,5-heptanedione [I; Ar is 4-CH$_3$OOCC$_6$H$_4$, Alk is (CH$_2$)$_{10}$, R and R' are CH$_3$CH$_2$CO], colorless solid, m.p. 71°-72°–72°C.

Anal. Calcd for C$_{25}$H$_{38}$O$_5$: C, 71.74; H, 9.15. Found: C, 72.04; H, 9.19.

EXAMPLE 84 a. Ethyl 4-benzyloxyphenoxyacetate.

A mixture of 40 g. of 4-benzyloxyphenol, 45.8 g. of ethyl bromoacetate, 40.0 g. of potassium carbonate, 2 g. of potassium iodide and 400 ml. of acetone was heated at reflux for 24 hours. The reaction mixture was filtered and concentrated in vacuo, and the residue was recrystallized from an ether-petroleum ether mixture to give 50 g. of ethyl 4-benzyloxyphonoxyacetate, m.p. 72°–73° C.

b. Ethyl 4-hydroxyphenoxyacetate.

Ethyl 4-benzyloxyphenoxyacetate (5.8 g.) was hydrogenated in the presence of 0.5 g. of palladium-on-carbon catalyst in 200 ml. of absolute ethanol. There was obtained 4.00 g. of ethyl 4-hydroxyphenoxyacetate, m.p. 124°–125° C. when recrystallized from isopropyl alcohol.

c. Ethyl 3-chloro-4-hydroxyphenoxyacetate.

To 29 g. of ethyl 4-hydroxyphenoxyacetate in 50 ml. of chloroform was added at 0° C. 20.2 g. of sulfuryl chloride (sp. gr. 1.667) in 20 ml. of chloroform over a period of one hour. The reaction mixture was held for 1 hour at 0° C., then allowed to warm to room temperature and stirred for 20 hours. The product obtained by evaporation of the solvent was recrystallized from petroleum ether to give 30 g. of ethyl 3-chloro-4-hydroxyphenoxyacetate, m.p. 80°–82° C.

d. 2-Chloro-4-(2-hydroxyethoxy)phenol.

Ethyl 3-chloro-4-hydroxyphenoxyacetate (11.5 g.) in 300 ml. of absolute ether was added over a 90 minute period to a suspension of 3.0 g. of lithium aluminum hydride in 500 ml. of absolute ether held at reflux. The reaction mixture was warmed at reflux for five hours, then cooled and treated with dilute sulfuric acid. The ether layer was washed with water, dried over anhydrous magnesium sulfate and concentrated to give 8.5 g. of product, m.p. 76°–82° C. The latter was recrystallized from an isopropyl alcohol-petroleum ether mixture to give 5 g. of 2-chloro-4-(2-hydroxyethoxy)-phenol, m.p. 89°–90° C.

e. 4-{6-[2 - Chloro - 4 - (2 - hydroxyethoxy)phenoxy]hexyl}-3,5-heptanedione [I; Ar is 2-Cl-4-HOCH$_2$CH$_2$OC$_6$H$_3$, Alk is (CH$_2$)$_6$, R and R' are CH$_3$CH$_2$CO] was prepared from 9.0 g. of 2-chloro-4-(2-hydroxyethoxy)phenol, 14.6 g. of 4-(6-bromohexyl)-3,5-heptanedione, 6.9 g. of anhydrous potassium carbonate, 0.8 g. of potassium iodide and 420 ml. of acetone, two days at reflux. The product was isolated to give 19 g. of 4-{6-[2-(chloro - 4 - (2 - hydroxyethoxy)phenoxy]hexyl}--3,5-heptanedione as a yellow oil.

EXAMPLE 85

4-[6-(4-Sulfonphenoxy)hexyl]-3,5-heptanedione [I; Ar is 4-HO$_3$SC$_6$H$_4$, Alk is (CH$_2$)$_6$, R and R' are CH$_3$CH$_2$CO].

A mixture of 10.2 g. of 4-(6-phenoxyhexyl)-3,5-heptanedione (Example 5) and 2.13 ml. of concentrated sulfuric acid was heated on a steam bath for one hour. The reaction mixture was cooled, ice added, and the solution neutralized with aqueous potassim hydroxide. The solid product which formed was collected by filtration, washed with cold water and recrystallized from water to give 5.6 g. of 4-[6-(4-sulfophenoxy)hexyl]-3,5-heptanedione in the form of its potassium salt, m.p. 260° C.

Anal. Calcd for C$_{19}$H$_{27}$KO$_6$S: C, 53.09; H 6.51; S, 7.25. Found: C, 52.90; H, 6.53; S, 7.22.

We claim:

1. A compound of the formula

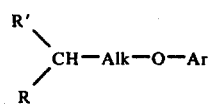

wherein:
Alk is alkylene of 3 to 10 carbon atoms optionally interrupted by an oxygen atom separated by at least two carbon atoms from the terminal bonds of Alk;
R and R' are alkanoyl of 2 to 6 carbon atoms;
and Ar is phenyl or phenyl substituted by one to three substituents selected from the group consisting of alkyl of 1 to 4 carbon atoms, alkoxy of 1 to 4 carbon atoms, alkylthio of 1 to 4 carbon atoms, alkoxyalkoxy of 3 to 6 carbon atoms, hydroxyalkoxy of 2 to 4 carbon atoms, halogen, nitro, acetyl, trifluoromethyl, trifluoromethoxy, hydroxy, and benzyloxy.

2. A pharmaceutically acceptable metal chelate of a compound according to claim 1.

3. A compound according to claim 1 wherein Alk is straight chain alkylene of 3 to 10 carbon atoms.

4. A compound according to claim 1 wherein R and R' are both propionyl and Alk is straight chain alkylene of 3 to 10 carbon atoms.

5. A compound according to claim 1 wherein Alk is straight chain alkylene of 3 to 10 atoms and Ar is 4-hydroxyphenyl.

6. 4-[6-(4-Hydroxyphenoxy)hexyl]-3,5-heptanedione, according to claim 5.

7. 4-[7-(4-Hydroxyphenoxy)heptyl]-3,5-heptanedione, according to claim 5.

8. 4-[10-(4-Hydroxyphenoxy)decyl]-3,5-heptanedione, according to claim 5.

9. A compound according to claim 1 wherein Alk is straight chain alkylene of 3 to 10 carbon atoms and Ar is 4-benxyloxyphenyl.

10. 4-[6-(4-Benxyloxyphenoxy)hexyl]-3,5-heptanedione, according to claim 9.

11. 4-[7-(4-Benzyloxyphenoxy)heptyl]-3,5-heptanedione, according to claim 9.

12. 4-[6-(2-Chloro-4-benzyloxyphenoxy)hexyl]-3,5-heptanedione, according to claim 9.

13. A compound according to claim 1 wherein Alk is straight chain alkylene of 3 to 10 carbon atoms and Ar is halophenyl.

14. 4-[6-(4-Chlorophenoxy)hexyl]-3,5-heptanedione, according to claim 13.

15. 4-[6-(2-Fluorophenoxy)hexyl]-3,5-heptanedione, according to claim 13.

16. 4-[6-(2-Chlorophenoxy)hexyl]-3,5-heptanedione, according to claim 13.

17. 4-[6-(4-Iodophenoxy)hexyl]-3,5-heptanedione, according to claim 13.

18. 4-[6-(4-Fluorophenoxy)hexyl]-3,5-heptanedione, according to claim 13.

19. A compound according to claim 1 wherein Alk is straight chain alkylene of 3 to 10 carbon atoms and Ar is alkoxyphenyl.

20. 4-[6-(4-Methoxyphenoxy)hexyl]-3,5-heptanedione, according to claim 19.

21. A compound according to claim 1 wherein Alk is straight chain alkylene of 3 to 10 carbon atoms and Ar is phenyl.

22. 4-(6-Phenyloxyhexyl)-3,5-heptanedione, according to claim 21.

23. A compouhd according to claim 1 wherein Alk is straight chain alkylene of 3 to 10 carbon atoms and Ar is 2-chloro-4-methoxyphenyl.

24. 4-[6-(2-Chloro-4-methoxyphenoxy)hexyl]-3,5-heptanedione, according to claim 23.

25. 4-[7-(2-Chloro-4-methoxyphenoxy)heptyl]-3,5-heptanedione, according to claim 23.

26. 3-[7-(2-Chloro-4-methoxyphenoxy)heptyl]-2,4-pentanedione, according to claim 23.

27. 4-[6-(2-Chloro-4-methoxyphenoxy)hexyl]-2,2,6,6-tetramethyl-3,5-heptanedione, according to claim 23.

28. 4-[8-(2-Chloro-4-methoxyphenoxy)octyl]-3,5-heptanedione, according to claim 23.

29. A compound according to claim 1 wherein Alk is straight chain alkylene of 3 to 10 carbon atoms and Ar is nitrophenyl.

30. 4-[6-(4-Nitrophenoxy)hexyl]-3,5-heptanedione, according to claim 29.

31. 4-[6-(2Nitrophenoxy)hexyl]-3,5-heptanedione, according to claim 29.

32. 4-[6-(2-Bromo-4-methoxyphenoxy)hexyl]-3,5-heptanedione, according to claim 4.

33. 4-[6-(3-Chloro-5-metnoxyphenoxy)hexyl]3,5-heptanedione, according to claim 4.

34. 4-[6-(4-Bromo-2-chlorophenoxy)hexyl]-3,5-heptanedione, according to claim 4.

35. 4-[6-(2-Chloro-4-fluorophenoxy)hexyl]-3,5-heptanedione, according to claim 4.

36. 4-[6-(2-Trifluoromethylphenoxy)hexyl]-3,5-heptanedione, according to claim 4.

37. 4-[6-(2,4,6-Triiodophenoxy)hexyl]-3,5-heptanedione, according to claim 4.

38. 4-[6-(2,5-Dichloro-4-methoxyphenoxy)hexyl]-3,5-heptanedione, according to claim 4.

39. 4-[6-(4-Methylthiophenoxy)hexyl]-3,5-heptanedione, according to claim 4.

40. 4-[6-(4-Methoxy-2-nitro)hexyl]-3,5-heptanedione, according to claim 4.

41. 4-[6-(2,3,4,5,6-Pentafluoro)hexyl]-3,5-heptanedione.

42. A composition for combatting arthropods by hindering their maturation which comprises an effective amount of at least one compound according to claim 1 in admixture with a suitable carrier or diluent.

43. A method for combatting arthropods by hindering their maturation which comprises treating said arthropods at any stage of their development with an effective amount of at least one compound according to claim 1 in admixture with a suitable carrier or diluent.

44. A composition for combatting viruses which comprises an antivirally effective amount of at least one compound according to claim 1 in admixture with a suitable carrier or diluent.

45. A composition according to claim 44 wherein the antivirally effective compound is 4-[6-(2-chloro-4-methoxyphenoxy)hexyl]-3,5-heptanedione.

46. A method for combatting viruses which comprises contacting the locus of said viruses with a composition containing an antivirally effective amount of at least one compound according to claim 1 in admixture with a suitable carrier or diluent.

47. A method according to claim 46 wherein the antivirally effective compound is 4-[6-(2-chloro-4-methoxyphenoxy)hexyl]-3,5-heptanedione.

* * * * *

UNITED STATES PATENT AND TRADEMARK OFFICE
CERTIFICATE OF CORRECTION

PATENT NO. : 4,031,246
DATED : June 21, 1977
INVENTOR(S) : Joseph C. Collins and Guy D. Diana It is certified that error appears in the above-identified patent and that said Letters Patent are hereby corrected as shown below:

Column 3, line 28, "RR'CM$^-$M$^+$" should read --RR'CH$^-$M$^+$--.

Column 4, line 30, "RR'$\lambda$" should read --RR'--.

Column 5, line 46, "paraninfluenza" should read --parainfluenza--.

Column 6, line 54, "sprays as" should read --sprays or--.

Column 7, line 8, "unreacted" should read --Unreacted--; line 33, "diethylformamide" should read --dimethylformamide--.

Column 8, line 57, "distilling" should read --distilled--.

Column 9, delete line 35; line 36, after "In" insert --vivo activity--.

Column 25, line 61, Claim 5, before "atoms" insert --carbon--.

UNITED STATES PATENT AND TRADEMARK OFFICE
CERTIFICATE OF CORRECTION

PATENT NO. : 4,031,246

DATED : June 21, 1977

INVENTOR(S) : Joseph C. Collins and Guy D. Diana

It is certified that error appears in the above-identified patent and that said Letters Patent are hereby corrected as shown below:

Column 26, line 3, Claim 9, "benxyloxyphenyl" should read --benzyloxyphenyl--; line 4, Claim 10, "Benxyloxyphenoxy" should read --Benzyloxyphenoxy--; line 57, Claim 33, "metnoxyphenoxy)hexyl]3,5-" should read --methoxyphenoxy)hexyl]-3,5- --.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*